(12) United States Patent
Pieroni et al.

(10) Patent No.: US 6,431,350 B1
(45) Date of Patent: Aug. 13, 2002

(54) DENTAL MATERIAL PACKAGING

(75) Inventors: Robert J. Pieroni, Rehoboth Beach; Paul R. Pierson, Camden, both of DE (US); Alain Damaiś, Northvale, NJ (US)

(73) Assignee: Dentsply Research & Development Corp.

( * ) Notice: Subject to any disclaimer, the term of this patent is extended or adjusted under 35 U.S.C. 154(b) by 0 days.

(21) Appl. No.: 09/791,043

(22) Filed: Feb. 22, 2001

(51) Int. Cl.[7] .............................................. A61B 19/02
(52) U.S. Cl. ........................................ 206/63.5; 211/74
(58) Field of Search ................................ 206/63.5, 446, 206/222; 211/74, 85.13; 422/102, 104

(56) References Cited

U.S. PATENT DOCUMENTS

| | | | |
|---|---|---|---|
| 2,469,763 A | 5/1949 | Conwell | 132/12 |
| 2,803,252 A | 8/1957 | Bloome | 128/303 |
| 3,347,410 A * | 10/1967 | Schwartzman | 222/80 |
| 3,521,745 A * | 7/1970 | Schwartzman | 206/222 |
| 3,731,853 A | 5/1973 | Baumann | 222/386 |
| 3,739,847 A | 6/1973 | Reynolds | 166/107 |
| 3,818,911 A | 6/1974 | Fournier | 128/269 |
| 3,968,872 A | 7/1976 | Cavazza | 206/222 |
| 4,167,228 A | 9/1979 | Cheetham | 206/222 |
| 4,195,731 A | 4/1980 | Cavazza | 206/222 |
| 4,294,351 A | 10/1981 | Cheetham | 206/222 |
| 4,643,674 A * | 2/1987 | Zdarsky | 433/102 |
| 4,717,057 A * | 1/1988 | Porteous | 224/217 |
| 4,786,534 A | 11/1988 | Aiken | 428/34.2 |
| 4,795,211 A * | 1/1989 | Stern et al. | 297/194 |
| 4,844,308 A * | 7/1989 | Porteous | 224/217 |
| 5,098,297 A | 3/1992 | Chari et al. | 433/215 |
| 5,112,152 A | 5/1992 | McBride | 401/132 |
| 5,184,719 A | 2/1993 | Gordon | 206/209.1 |
| 5,290,261 A * | 3/1994 | Smith, Jr. et al. | 604/234 |
| 5,372,177 A | 12/1994 | Foster | 164/35 |
| 5,440,774 A | 8/1995 | Cole | 15/15 |
| 5,660,273 A | 8/1997 | Discko, Jr. | 206/229 |
| 5,860,806 A | 1/1999 | Pranitis, Jr. et al. | 433/80 |
| 6,036,490 A * | 3/2000 | Johnsen et al. | 433/102 |
| 6,082,997 A * | 7/2000 | Prescott | 433/49 |

FOREIGN PATENT DOCUMENTS

EP 0 271 976 6/1988

OTHER PUBLICATIONS

Exhibit "A" Advertisement for package for dental material.
Exhibit "B" Advertisement for package for dental material.
Exhibit "C" Advertisement for package for dental material.
Exhibit "D" Advertisement for package for dental material.
Exhibit "E" Advertisement for package for dental material.
Exhibit "F" Advertisement for package for dental material.
Exhibit "G" Advertisement for package for dental material.
Exhibit "H" Advertisement for package for dental material.
Exhibit "I" Directions for use for dental package.

* cited by examiner

*Primary Examiner*—Mickey Yu
*Assistant Examiner*—Jila M. Mohandesi
(74) *Attorney, Agent, or Firm*—Douglas J. Hura; James B. Bieber

(57) ABSTRACT

The invention provides a storage stable dental composition having a volatile organic solvent and a polymerizable material enclosed by a package, which includes a cover and a container made of a polymer such as a copolymer of a cycloolefin and an open chain olefin. In accordance with an embodiment of the invention is provided a stored packaged dental product by the process including: enclosing a dental composition in a package with at least a substantial portion of an injection molded polymer such as a thermoplastic copolymer of a cycloolefin and an open chain olefin, and storing the dental composition in the package for a least 1 week.

4 Claims, 2 Drawing Sheets

DENTAL MATERIAL PACKAGING

The invention relates to packaged dental compositions and methods of use thereof. The invention provides a storage stable packaged dental composition having one or more volatile components and methods of use thereof. In accordance with the invention there is provided a storage stable packaged dental compositions having one or more volatile components such a polar organic solvent and/or low molecular weight monomer.

One major problem with prior art injection molded packaging of dental compositions having one or more volatile components is the loss of a major portion of the volatile components from the dental compositions during storage. When the stored dental compositions with effectively reduced volatile components are used the originally available results are not provided. Thus, for example, dental adhesive and/or primer compositions stored in prior art injection molded packaging loose much, if not all, of their capacity for adhesion and/or priming. Other problems with prior art injection molded packaging of dental compositions include weight decrease of the polymeric material while enclosing the dental composition due to diffusion of components of the polymeric material from the polymeric material, and may cause contamination of the dental composition by components of the polymeric material. A weight increase of the polymeric material while enclosing the dental composition may be due to infusion of water from ambient humidity and/or solvent (or other components) from the polymeric material. Thus a weight increase of the polymeric material may be indicative of a loss of solvent from the dental composition and/or water contamination of the dental composition. When the stored dental compositions (with effectively contaminated and/or depleted components) are used, the originally available results are not provided. These problems of prior art injection molded packaging of dental compositions are solved by the present invention.

BACKGROUND OF THE INVENTION

To ensure proper functioning of dental materials, they need to be protected from undergoing changes during storage. These changes of material may occur if external substances (e.g. moisture) penetrate the dental materials, or if parts of the dental materials (e.g. solvents) evaporate or otherwise diffuse off. Therefore a suitable packaging is needed to prevent both intrusion of moisture into the dental materials and evaporation of solvent or other vital parts of the dental materials. Several ways of packaging have been tried, mostly using laminate materials consisting of different polymers. However, particularly for very small containers of dental materials (e.g. single unit dosage containers), laminate materials are not a viable solution as they are too difficult to shape and process.

It is an object of the invention to provide a storage stable dental composition such as one containing a volatile organic solvent and a polymerizable material enclosed by a package, which includes a cover and a container.

It is an object of the invention to provide a stored packaged dental product by the process including: enclosing a dental composition in a package with at least a substantial portion of an injection molded polymer, and storing the dental composition in the package for at least 1 week.

It is an object of the invention to provide a stored packaged dental product by the process comprising: enclosing a dental composition including a volatile organic solvent in a package, at least a substantial portion of the package comprising a polymer having a high chemical resistance and barrier capability toward polar organic solvents and water. After storing the dental composition in the package for at least two weeks at 37° C. at least 50 and more preferably 75 or even 90 percent of the volatile organic solvent remains in the package.

As used herein open chain olefins are noncyclic olefins and include linear open chain olefins, straight chain olefins, branched chain olefins and branched open chain olefins. Open chain olefins are not closed chain olefins or ring olefins. Linear open chain olefins are most preferred open chain olefins for use in making copolymer for use in accordance with the invention.

As used herein volatile component refers to a component (of a dental composition) having vapor pressure more than that of water at 20° C.

As used herein volatile polar solvents refers to polar solvents, such as water, ethanol and acetone, which are at least as volatile as water at 20° C.

As used herein volatile organic solvents refers to organic solvents, such as ethanol and acetone, which are more volatile than water at 20° C.

As used herein moderately volatile organic solvent refers to an organic solvent, such as ethanol, which is more volatile than water, but not more volatile than ethanol i.e. vapor pressure more than that of water at 20° C., but less than or equal to 43 mm Hg at 20° C.

As used herein very volatile organic solvent refers to an organic solvent, such as acetone, which is more volatile than ethanol i.e. vapor pressure more than 43 mm Hg at 20° C.

As used herein high permeability barrier capability for water (and high water barrier capability) refers to polymeric material having a water vapor permeability below 0.07 g $(mm)(m^{-2})(d^{-1})$ measured by DIN 53122 at 23° C. and 85 percent relative humidity.

As used herein high penetration barrier capability for solvent of a polymeric material toward polar organic solvents refers to less than 2 percent by weight loss of polar organic solvents from a composition having at least 5 percent by weight of polar organic solvent(s) while enclosed in the polymeric material for at least two weeks at 37° C.

As used herein very high penetration barrier capability for solvent of a polymeric material toward polar organic solvents refers to less than 0.5 percent by weight loss of polar organic solvents from a composition having at least 5 percent by weight of polar organic solvent(s) while enclosed in the polymeric material for at least two weeks at 37° C.

As used herein high penetration barrier capability for water of a polymeric material toward water and humidity refers to a less than 3 percent by weight increase of a composition due to infusion of water through the polymeric material while the composition is enclosed in the polymeric material for at least two weeks at 37° C.

As used herein very high penetration barrier capability for water of a polymeric material toward water and humidity refers to a less than 1 percent by weight increase of a composition due to infusion of water through the polymeric material while the composition is enclosed in the polymeric material for at least two weeks at 37° C.

As used herein high chemical resistance of polymeric material refers to polymeric material having both a less than 3 percent by weight increase of the polymeric material, and a less than 0.5 percent by weight decrease of the polymeric material while the polymeric material is immersed in water and/or solvent for at least two weeks at 37° C. A weight decrease of the polymeric material while enclosing a dental composition (and/or immersed in water and/or solvent) may be due to diffusion of components of the polymeric material from the polymeric material, and may cause contamination of the dental composition by components of the polymeric material. A weight increase of the polymeric material while enclosing a dental composition and/or immersed in water and/or solvent may be due to infusion of water and/or solvent into the polymeric material, and may indicate that the polymeric material allows loss (or gain) of solvent from the dental composition and/or water contamination of a dental composition.

As used herein low molecular weight monomer refers to an acrylic monomer, such as methyl methacrylate having a gram molecular weight less than 150.

As used herein single unit dosage refers to volumes of a dental composition between 0.01 and 1 ml.

SUMMARY OF THE INVENTION

Figure 1:
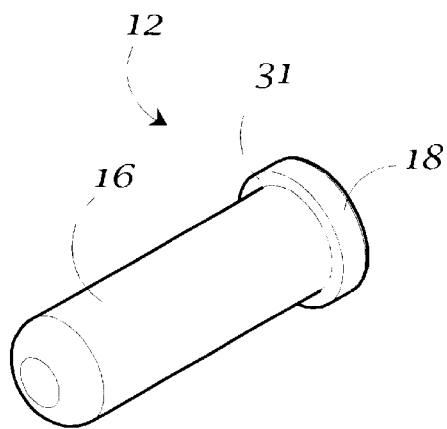
FIG. 1 is a perspective view of a covered container in accordance with the invention.

The invention provides a storage stable dental composition comprising for example a volatile organic solvent and/or a polymerizable material enclosed by a package, which includes a cover and a container made of a polymer such as a copolymer of a cycloolefin and an olefin. Preferably a thermoplastic polymeric packaging made of a copolymer of a cycloolefin and an open chain olefin is used. This packaging material combines ease of processing by injection-molding with properties giving protection of the dental materials by high barrier capability and chemical resistance to water and polar organic solvents, such as acetone. Furthermore, containers made from this packaging material may be sealed by thermal welding with a laminate plastic foil. The invention provides a stored packaged dental product by the process comprising: enclosing a dental composition in a package, at least a substantial portion of the package comprising thermoplastic polymer having a high barrier capability and chemical resistance to water and polar organic solvents. Preferably the thermoplastic polymer has high penetration barrier capability for solvent toward polar organic solvents and a high water barrier capability. After storing the dental composition in the package for at least two weeks at 37° C. at least 50, preferably 75 and most preferably 90 percent of the volatile organic solvent remains in the package.

The invention to provide a stored packaged dental product by the process including: enclosing a dental composition in a package with at least a substantial portion of an injection molded polymer, such as a thermoplastic copolymer of a cycloolefin and an open chain olefin, and storing the dental composition in the package for at least 1 week.

DETAILED DESCRIPTION OF THE INVENTION

The invention is now described in reference to FIGS. 1 through 8. With more particular reference to FIGS. 1 through 5 is seen storage stable dental composition packaging system 10 having a package 12 and a volatile dental composition 14. The volatile dental composition 14 is enclosed by package 12. Package 12 includes container 16 and cover 18. Container 16 is made of polymer such as a copolymer of a cycloolefin and an olefin. Dental composition 14 comprises for example a volatile organic solvent and a polymerizable material. The storage stable dental composition packaging system is stored for weeks, months or even years without significant loss of volatile organic solvent from dental composition 14 in closed package 12. In use container 16 is placed in holder 20 and uncovered for use by pealing or puncturing cover 18 from container 16. The user dispenses dental material by dipping a dental applicator (not shown) into uncovered container 16, for example while container 16 is supported in a holder 20.

Figure 2:
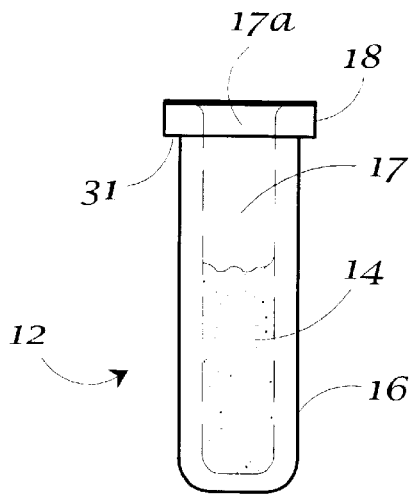
FIG. 2 is a side elevational view of the container of FIG. 1 showing an internal chamber in phantom lines.
Figure 3:
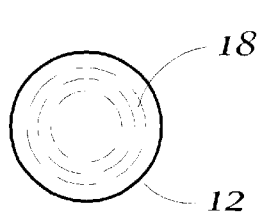
FIG. 3 is a top plan view of the container shown in FIG. 1.
Figure 4:
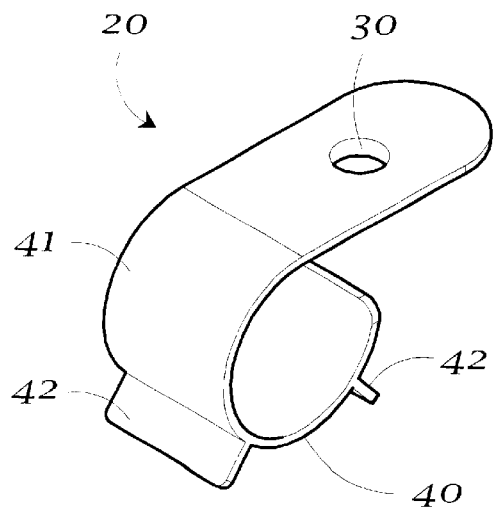
FIG. 4 is a perspective view of a folder or stand for use with the container of FIG. 1.
Figure 5:
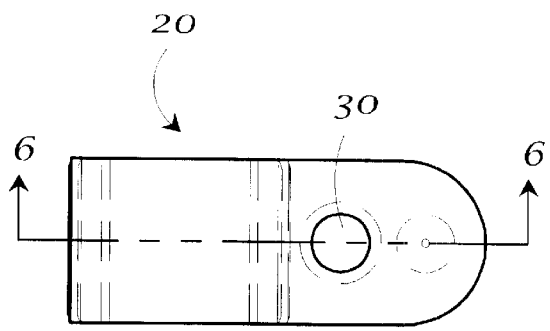
FIG. 5 is a top plan view of the holder shown in FIG. 4.
Figure 6:
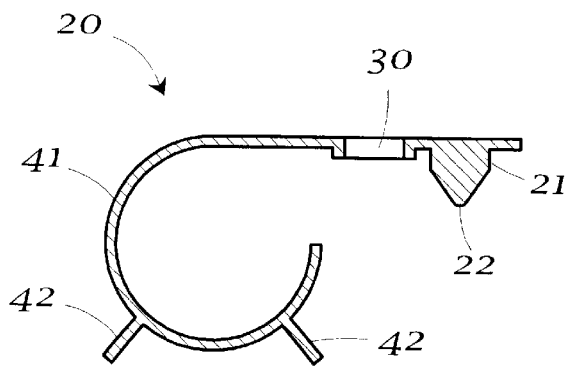
FIG. 6 is a side, cross-sectional view taken along line 6—6 of FIG. 5.
Figure 7:
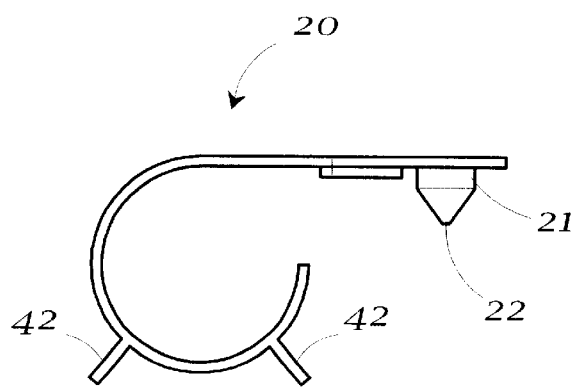
FIG. 7 is a side elevational view of the holder of FIG. 4.
Figure 8:
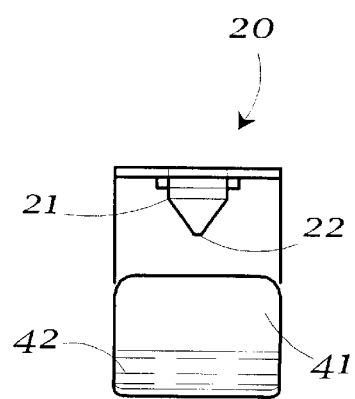
FIG. 8 is a front elevational view of the holder of FIG. 4.

As will be further discussed below, container 16 has an interior chamber 17 which, as shown in FIG. 2, holds dental composition 14. Chamber 17 has an open top 17a which is closed by cover 18. Cover 18 may be a laminate foil which is bonded to container 16, or cover 18 may be formed from the same material as container 16, or other suitable plastic material and affixed to open end 17a of container 16. In use, in order to obtain access to chamber 17 and hence to dental composition 14, it is merely necessary to remove cover 18, or more preferably, puncture cover 18 with a suitable device.

Exemplary thermoplastic polymeric cycloolefin- olefin-copolymer useful for storage stable packaging of dental composition in accordance with the invention are disclosed in EP 407,870; EP 156,464 and EP 283,164. Thus each discloses copolymers of cycloolefin and olefin useful for making containers and covers for use in accordance with the invention. The disclosures of EP 407,870; EP 156,464 and EP 283,164 are each hereby incorporated herein by reference each in its entirety.

Copolymer of cycloolefin and open chain olefin useful for storage stable packaging of dental composition in accordance with the invention have the following properties: thermoplasticity, suitable for injection-molding, high moisture-barrier capability, high barrier capability towards organic solvents, high chemical resistance, high rigidity, and suitability for sealing with laminate foil via thermal welding or ultrasonic welding. Preferred copolymers of cycloolefin and open chain olefin for use in accordance with a preferred embodiment of the invention are copolymers of norbornene and ethylene for example the norbornene-ethylene-copolymer sold by Ticona GmbH as Topas 6013. Topas 6013 norbornene-ethylene-copolymer has the following properties: thermoplasticity, can be processed on conventional injection molding machines; high moisture vapour barrier: permeability of 0.035 (g)(mm/m$^2$)(24 hours) at 23° C., 85% relative humidity, high barrier capability towards polar organic solvents such as acetone, high resistance towards water, strong acids and bases, and polar organic solvents such as methanol, ethanol and acetone, high rigidity: yield stress of 66 MPa, tensile modulus of 3200 MPa and suitable for sealing with laminate foil via thermal welding.

In accordance with a preferred embodiment of the invention is provided a storage stable dental composition comprising a volatile organic solvent and a polymerizable material enclosed by a package, which includes a cover and a container comprising a copolymer of a cycloolefin and an olefin. Preferably the package has an open end 17A sealed closed by a cover 18. Preferably the packaged dental composition is stored at about 23° C. for at least one year and at least about 50, more preferably about 70 and most preferably about 80 percent of the volatile organic solvent remains in the package. Preferably the storage stable packaged dental composition is stored at about 23° C. for at least two years and at least about 50, more preferably 75 and most preferably about 90 percent of the volatile organic solvent remains in the package. Preferably the storage stable packaged dental composition is stored at about 23° C. for at least two years and at least about 50, more preferably about 75 and most preferably about 95 percent of the volatile organic solvent remains in the package. Preferably the volatile organic solvent of the storage stable packaged dental composition comprises acetone. Preferably the storage stable packaged dental composition is at least 20 percent by weight acetone both before and after storage at about 23° C. for two years and at least 95 percent of the volatile organic solvent remains in the package after the storage. Preferably the storage stable packaged dental composition is at least 20 percent by weight acetone both before and after storage at about 23° C. for one year and at least 90 percent of the acetone remains in the package after the storage. Preferably the storage stable packaged dental composition is at least 40 percent by weight acetone both before and after storage at about 23° C. for two years and at least 95 percent of the volatile organic solvent remains in the package after the storage. Preferably the storage stable packaged dental composition is at least 40 percent by weight acetone both before and after storage at about 23° C. for one year and at least 90 percent of the acetone remains in the package after the storage. Preferably the storage stable packaged dental composition is at least 50 percent by weight acetone both before and after storage at about 23° C. for two years and at least 95 percent of the volatile organic solvent remains in the package after the storage. Preferably the storage stable packaged dental composition is at least 50 percent by weight acetone both before and after storage at about 23° C. for one year and at least 90 percent of the acetone remains in the package after the storage.

In accordance with a preferred embodiment of the invention is provided a storage stable packaged dental composition wherein the dental composition comprising a solvent and a polylmerizable material is enclosed by a container comprising a polymer such as a copolymer of a cycloolefin and an olefin, the dental composition, the packaged dental composition is at least 10 percent by weight solvent both before and after storage at about 43° C. for one week, and at least 99 percent of the solvent remains in the package after storage. Preferably at least 99.5 percent of the solvent remains in the package after storage. More preferably at least 99.8 percent of the solvent remains in the package after storage. Most preferably the solvent is a volatile organic solvent and at least 99.9 percent of the solvent remains in the package after storage.

In accordance with a preferred embodiment of the invention is provided a method of storing polymerizable material, comprising: providing a dental composition and a package, the package substantially enclosing the dental composition, the dental composition comprising a polar organic solvent at least a portion of the package comprising a thermoplastic polymer comprising a copolymer of a cycloolefin and an olefin and having a high penetration barrier capability for water and solvent and high chemical resistance, whereby when the dental composition is stored at about 23° C. in the package for at least two years and at least 90 percent of the polar organic solvent remains in the package. Preferably the dental composition, initially comprises at least 10 percent by weight of the solvent before storage at about 43° C. for one week and at least 99 percent of the solvent remains in the package after the storage. More preferably the dental composition, initially comprises at least 15 percent by weight of solvent before storage at about 43° C. for one week and at least 99.8 percent of the solvent remains in the package after storage.

In accordance with a preferred embodiment of the invention is provided a packed dental product, comprising: a package substantially enclosing a dental composition comprising a solvent. The package comprising a container and a cover. At least a portion of the container comprises a thermoplastic copolymer of a cycloolefin and an olefin and having a high permeability barrier capability for water and high chemical resistance. The cover comprises a metal foil. When the dental composition is stored at about 23° C. in the package for at least two years and at least 99 percent of the dental composition remains in the package.

The cover 18 may comprise a polymeric film, such as polyethylene or polypropylene laminated to the metal foil. Preferably the cover comprises a molded member, sheet, film or coating of thermoplastic polymer comprising a copolymer of a cycloolefin and an olefin and having a high permeability barrier capability for water and high chemical resistance. Preferably the container is injection molded. Preferably the package has a longest dimension less than 4 cm. Preferably the container has a longest dimension less than 2 cm. Preferably the cover comprises a thermoplastic polymer comprising a copolymer of a cycloolefin and an open chain olefin and having a high permeability barrier capability for water and high chemical resistance towards both water and the solvent. Preferably the copolymer has a permeability to water of less than 0.07 $(g)(mm/m^2)(24$ hours) at 23° C. and 85% relative humidity. More preferably the copolymer has a permeability to water of less than 0.05 $(g)(mm/m^2)(24$ hours) at 23° C. and 85% relative humidity.

In accordance with a preferred embodiment of the invention is provided a stored packaged dental product by the process comprising: enclosing a dental composition in a package, at least a substantial portion of the package comprising thermoplastic polymer having a high resistance toward polar organic solvents and a high water barrier capability, and storing the dental composition in the package for at least two weeks at 37° C. and after the two weeks at least 90 percent of the volatile organic solvent remains in the package. Preferably the package includes a molded portion and a laminated portion. Preferably the package is made by sealing a molded portion to a laminated portion. Preferably the thermoplastic polymer of the molded portion is injection molded and has an average thickness from about 0.4 mm to about 6 mm. More preferably the injection molded thermoplastic polymer has an average thickness from about 0.6 mm to about 4 mm. Most preferably the injection molded thermoplastic polymer has an average thickness from about 0.8 mm to about 3 mm. Preferably the thermoplastic polymer is a copolymer of a cycloolefin and an open chain olefin. The open chain olefin is preferably a straight open chain olefin or a branched open chain olefin. The open chain olefin of the copolymer used to mold at least a portion of the package, preferably has a gram molecular weight which is less than half of the gram molecular weight of the cycloolefin of the copolymer. Preferably the package has a cover over a readily opened end, and the cover comprises a polymeric film, such as polyethylene or polypropylene laminated to the metal foil such as aluminum foil.

In accordance with a preferred embodiment of the invention is provided a dental method of use, of a thermoplastic polymer, having a high permeability barrier capability for water, high chemical resistance, as at least a substantial portion of a package enclosing a dental composition comprising at least 3 percent by weight of volatile organic solvent, whereby the dental composition is stored in the package at about 23° C. for at least two years and after the two years at least 90 percent of the volatile organic solvent remains in the package. Preferably the dental composition comprises at least 5 percent by weight of volatile organic solvent. More preferably the dental composition comprising at least 10 percent by weight of volatile organic solvent.

Cover 18 may be peeled or otherwise removed if it is a foil or other flexible closure for open end 17a of container 16. As discussed above, cover 18 may also be formed from a plastic, relatively hard material, such as the same material forming container 16. Cover 18 may be punctured by any means, such as any handy or available dental instrument (not shown).

According to one embodiment of the invention, container 16 is placed in a holder 20 for use. Holder 20 may be fitted with a protrusion 21, which has a sharp end 22 which is useful for puncturing cover 18. Holder 20 is also provided with an aperture 30 wherein container 16 may be placed. Preferably, container 16 at open end 17a has a shoulder 31 which will physically engage holder 20 when container 16 is placed in aperture 30. Holder 20 is provided with a base portion 40 which may be formed from a rounded portion 41 integrally formed with the remaining portions of holder 20.

Holder 20 may also be provided with support legs 42 to support holder 20 upon a flat surface (not shown). Preferably, rounded portion 41 of holder 20 provides a center of mass somewhere contiguously within rounded portion 41, even when a full container 16 is placed within aperture 30. In this way, particularly with the use of support legs 42, container 16 will be held in a substantially upright position similar to that shown in FIG. 2, wherein container 16 is placed in aperture 30 and shoulders 31 of container 16 physically engage holder 20.

Various alterations and modifications of the invention will be apparent to those of ordinary skill in the art without departing from the scope and spirit of this invention. Accordingly, it should be understood that the invention is not limited to the illustrative embodiments set forth herein.

What is claimed is:

1. A storing and dispensing package for a dental material comprising in combination:

an openable, closed container and a support holder for said container; said container comprising an interior chamber and a sealed end, said sealed end being sealed with a cover; said container further comprising a shoulder proximate to said sealed end; said holder comprising a base portion, a puncture protrusion and a container receiving aperture, such that in use, said cover may be punctured with said puncture protrusion and then said container can be received in said aperture, whereby physical engagement between said holder and said shoulder supports said container within said aperture and by said holder; said base portion being rounded and having support legs thereon; wherein when said container is received within said aperture, the center of gravity of said combination of said container and said holder is located within said rounded portion of said base portion.

2. A package as in claim 1, wherein said container is formed from a thermoplastic polymeric material.

3. A package as in claim 2, wherein said thermoplastic polymeric material is a copolymer of a cycloolefin and an olefin.

4. A method of dispensing a dental material comprising the steps of providing an openable, closed container and a support holder for said container; said container comprising an interior chamber and a sealed end, said sealed end being sealed with a cover; said container further comprising a shoulder proximate to said sealed end; said holder comprising a base portion, a puncture protrusion and a container receiving aperture; and puncturing said cover by physical contact with said puncture protrusion, placing said container in said aperture, such that physical engagement between said holder and said shoulder supports said container within said aperture and by said holder; and wherein said base portion being rounded and having support legs thereon; wherein when said container is received within said aperture, the center of gravity of said combination of said container and said holder is located within said rounded portion of said base portion.

* * * * *